United States Patent
Balschat et al.

(10) Patent No.: US 9,511,182 B2
(45) Date of Patent: Dec. 6, 2016

(54) MEDICAL TREATMENT ARRANGEMENT

(75) Inventors: Klaus Balschat, Schwebheim (DE);
Berthold Breitkopf, Schweinfurt (DE);
Klaus Sauer, Reuchelheim (DE);
Marcus Hartmann, Schweinfurt (DE);
Dejan Nikolic, Frankfurt (DE);
Alexander Heide, Eppstein (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 645 days.

(21) Appl. No.: 13/699,110

(22) PCT Filed: May 20, 2011

(86) PCT No.: PCT/EP2011/002532
§ 371 (c)(1),
(2), (4) Date: Nov. 20, 2012

(87) PCT Pub. No.: WO2011/144355
PCT Pub. Date: Nov. 24, 2011

(65) Prior Publication Data
US 2013/0062265 A1 Mar. 14, 2013

(30) Foreign Application Priority Data
May 20, 2010 (DE) .................. 10 2010 022 201

(51) Int. Cl.
*A61M 1/14* (2006.01)
*A61M 1/34* (2006.01)
(Continued)

(52) U.S. Cl.
CPC ............ *A61M 1/34* (2013.01); *A61M 1/1656* (2013.01); *A61M 1/1668* (2014.02); *A61M 1/28* (2013.01);
(Continued)

(58) Field of Classification Search
None
See application file for complete search history.

(56) References Cited

U.S. PATENT DOCUMENTS 4,229,299 A 10/1980 Savitz et al.
4,765,888 A 8/1988 Barthe et al.
(Continued)

FOREIGN PATENT DOCUMENTS

AU 4017885 9/1985
CN 1859936 11/2006
(Continued)

OTHER PUBLICATIONS

Armin Gärtner, "Medizinishce Netzerke und vernetzte medizinische Systeme—Teil 1", S. 169-173, Medizintechnik 129 (2009) Nr. 5, ISSN 0344-9416.
(Continued)

*Primary Examiner* — Krishnan S Menon
*Assistant Examiner* — Bradley R Spies
(74) *Attorney, Agent, or Firm* — Jacobson Holman, PLLC.

(57) ABSTRACT

The present invention relates to a medical treatment arrangement having at least three device parts, with the first device part being a device part which is not made for the treatment of a patient, with the second device part being made in conjunction with the third device part such that a treatment of a patient can be made with them, with the second device part being made movable relative to the first device part and relative to the third device part, and with provision furthermore being made that the first device part and the second device part and/or the second device part and the third device part being made such that energy and/or data can be unidirectionally or bidirectionally exchanged between them.

25 Claims, 22 Drawing Sheets

(51) Int. Cl.
*A61M 1/16* (2006.01)
*A61M 1/28* (2006.01)

(52) U.S. Cl.
CPC ...... *A61M 1/342* (2013.01); *A61M 2205/3569* (2013.01); *A61M 2205/3592* (2013.01); *A61M 2205/6054* (2013.01); *A61M 2205/6072* (2013.01); *A61M 2209/084* (2013.01)

(56) References Cited

U.S. PATENT DOCUMENTS

| | | | |
|---|---|---|---|
| 5,762,782 | A | 6/1998 | Kenley et al. |
| 5,914,047 | A | 6/1999 | Griffiths |
| 8,317,099 | B2 | 11/2012 | Perkins et al. |
| 8,671,996 | B2 | 3/2014 | Weilhoefer et al. |
| 2001/0044731 | A1* | 11/2001 | Coffman et al. ........... 705/3 |
| 2002/0023879 | A1 | 2/2002 | Hadden |
| 2003/0085684 | A1* | 5/2003 | Tsukamoto et al. ........ 320/108 |
| 2004/0176984 | A1* | 9/2004 | White et al. ............... 705/2 |
| 2005/0187529 | A1* | 8/2005 | Reasoner et al. ............ 604/317 |
| 2007/0060871 | A1* | 3/2007 | Istoc et al. ................. 604/65 |
| 2007/0135779 | A1 | 6/2007 | Lalomia et al. |
| 2008/0230450 | A1 | 9/2008 | Burbank et al. |
| 2008/0300658 | A1* | 12/2008 | Meskens .................. 607/60 |
| 2009/0012448 | A1* | 1/2009 | Childers et al. .............. 604/29 |
| 2009/0069784 | A1* | 3/2009 | Estes et al. ................ 604/500 |
| 2009/0322545 | A1 | 12/2009 | Gibson |
| 2010/0078092 | A1 | 4/2010 | Weilhoefer et al. |
| 2010/0093401 | A1* | 4/2010 | Moran ............... G06F 1/1626 455/566 |
| 2010/0137882 | A1 | 6/2010 | Jansson et al. |
| 2010/0204765 | A1 | 8/2010 | Hall et al. |
| 2011/0196279 | A1 | 8/2011 | Maiefhofer et al. |
| 2013/0001165 | A1 | 1/2013 | Pohlmeier et al. |

FOREIGN PATENT DOCUMENTS

| | | |
|---|---|---|
| CN | 101622021 | 1/2010 |
| CN | 102791305 | 11/2012 |
| DE | 1939923 | 5/1970 |
| DE | 9302790 | 6/1994 |
| DE | 19858158 | 4/1999 |
| DE | 10 2007 009269 | 8/2008 |
| DE | 10 2008 050849 | 4/2010 |
| EP | 0004600 | 10/1979 |
| EP | 1 543 853 | 6/2005 |
| JP | H1085322 | 4/1998 |
| JP | 2002536126 | 10/2002 |
| JP | 2008535569 | 9/2008 |
| WO | 9900154 | 1/1999 |
| WO | 01/64262 | 9/2001 |
| WO | WO 2004/062710 | 7/2004 |
| WO | WO 2006/108026 | 10/2006 |
| WO | WO 2007/048068 | 4/2007 |
| WO | WO 2008/082033 | 7/2008 |
| WO | 2008104367 | 9/2008 |

OTHER PUBLICATIONS

Armin Gärtner, "Medizinishe Netzwerke und vernetzte medizinische Systeme—Teil 2", Medizintechnik 129 (2009) Nr. 6, S. 213-217, ISSN 0344-9416.
Armin Gärtner, "Medizinishce Netzwerke Teil 3: Virtualisierung und shared network," Medizintechnik 130 (2010) Nr. 1, S. 13-19, ISSN 0344-9416.
Armin Gärtner, Funktrasponder 9RFID-Technologie) in der Medizintechnik, Medizintechnik 126 (2006) Nr. 4, S. 136-145, ISSN 0344-9416.
Armin Gärtner, "Medizinishce Netzerke und vernetzte medizinische Systeme—Teil 1", S. 169-173, Medizintechnik 129 (2009) Nr. 5, ISSN 0344-9416. (English abstract included).
Armin Gärtner, "Medizinishe Netzwerke und vernetzte medizinische Systeme—Teil 2", Medizintechnik 129 (2009) Nr. 6, S. 213-217, ISSN 0344-9416. (English abstract included).
Armin Gärtner, "Medizinishce Netzwerke Teil 3: Virtualisierung und shared network," Medizintechnik 130 (2010) Nr. 1, S. 13-19, ISSN 0344-9416. (English abstract included).
Armin Gärtner, Funktrasponder 9RFID-Technologie) in der Medizintechnik, Medizintechnik 126 (2006) Nr. 4, S. 136-145, ISSN 0344-9416 (English abstract included).
Drukker et al. Replacement of Renal Function by Dialysis. Hemodialysis Machines and Monitors, 1996, ISBN 0-7923-3610-0, S. 342-343.

* cited by examiner

Data are immediately transferred to the trolley

FULL
UNUSED
BAG ID

The display shows the data which were stored on the trolley

The display shows the data which were stored on the trolley

Data are immediately transferred to the trolley

EMPTY
USED
BAG ID

EMPTY
UNUSED
BAG ID

Data are immediately transferred to the RFID tag

FULL
UNUSED
AVAILABILITY
BAG ID

The display shows the data which are stored in the RFID tag

The bag data are read

FULL
UNUSED
BAG ID
AVAILABILITY

Data are immediately transferred to the RFID tag

FULL
USED
BAG ID

The display shows the data which are stored in the RFID tag

FULL
USED
BAG ID

Data are immediately transferred to the bag RFID tag

EMPTY USED BAG ID

BAG ID

Data are immediately transferred to the trolley

FULL
UNUSED
AVAILABILITY
BAG ID

The display shows the data which are stored in the trolley

The trolley data are read

FULL
UNUSED
BAG ID
AVAILABILITY

The data are immediately transmitted to the trolley

FULL
USED
BAG ID

The display shows the data which are stored in the trolley

FULL
USED
BAG ID

The data are immediately transferred to the trolley

EMPTY
USED
BAG ID

MEDICAL TREATMENT ARRANGEMENT

This is a national stage of PCT/EP11/002532 filed May 20, 2011 and published in German, which has a priority of German no. 10 2010 022 201.1 filed May 20, 2010, hereby incorporated by reference.

The present invention relates to a medical treatment arrangement having at least three device parts, with the first device part being a device part not adapted for the treatment of a patient and with the second device part being adapted in conjunction with the third device part such that a treatment of a patient can be carried out with them.

Dialyzers are known from the prior art in which the dialysis fluid is not manufactured during a treatment, but in which rather the total amount of dialysis fluid required for a dialysis treatment is provided in a tank prior to the treatment. Dialyzers of this type are also called "batch-type" dialyzers.

To fill the dialyzer with treatment fluid, it is conceivable to move said treatment fluid to the dialyzer by means of a mobile apparatus comprising a tank or any other container and to transfer the tank contents to the dialyzer so that the treatment of the patient is carried out using the treatment fluid. It is further conceivable in this respect that the tank or the other container of the mobile apparatus is previously filled with the treatment fluid from a filling station.

It is the underlying object of the present invention to enable a smooth interaction of the individual device parts with such a medical treatment arrangement comprising a plurality of device parts.

This object is satisfied by a medical treatment arrangement having the features of claim 1.

Provision is made in this respect that the second device part is made movable relative to the first device part and relative to the third device part and that the first and second device parts and/or the second and third device parts are made such that energy and/or data can be unidirectionally or bidirectionally exchanged between them.

It is thus possible, for example, for the initially named, non-restrictive example of a batch-type dialyzer that the second device part is a mobile apparatus having a tank or the like by means of which treatment fluid can be brought to the third device part, that is, to the dialyzer. With respect to the initially named embodiment, the first device part, which does not serve the treatment of the patient, can be a filling station and/or emptying station (in the following in part also only called a filling station) by means of which the tank of the second device part can be filled or emptied as desired.

Provision is now made in accordance with the invention that an exchange of data and/or of energy is possible between these device parts.

This has the advantage that, for example, information on the filling of the tank of the second device part can be stored, for example, in the second device part or in its tank and these data can then be read out from the third device part, that is, by the treatment device in accordance with the above embodiment. In this case, the second device part serves as a data transfer device between the first and third device parts.

The term "tank" is to be given a broad interpretation within the framework of the present invention and includes any container serving the reception of a fluid.

Provision is made in a preferred embodiment of the invention that the first device part and/or the third device part are made as immobile or substantially immobile. However, this is not absolutely necessary. If, for example, the third device part is a dialyzer, provision can be made that it is optionally also made as mobile. This also applies to other embodiments of the third device part.

Provision is preferably further made that the second device part is made as mobile and in particular has rollers, rolls or the like by means of which it can be moved. If the second device part is, for example, a mobile apparatus comprising a tank, the transfer of the treatment fluid from a filling station to a treatment device can be carried out by means of this mobile apparatus which can be moved by a user. It is generally also conceivable that the second device part is made as portable. This can, for example, be the case in peritoneal dialysis or also in the case of infusion devices in which the volumes of the fluid are comparatively small as a rule and the second device part can therefore also easily be made as portable.

Parallel to this transfer of the treatment fluid, it is conceivable that energy and/or data are additionally transferred, that is, that the second device part serves as an energy and/or data store and/or as an energy and/or data transfer device.

Provision is made in a further embodiment of the invention that the second device part is adapted in conjunction with the third device part such that a blood treatment process, in particular a dialysis process, in particular hemodialysis or peritoneal dialysis, can be carried out with them. These are, however, only examples in this respect. The following invention is not restricted to these treatment processes.

Provision is made in a further embodiment of the invention that at least one of the device parts, preferably a plurality of device parts or all device parts of the medical treatment arrangement, are designed such that the data transfer and/or the energy transfer takes place in a wireless or wired manner.

It is, for example, conceivable that a data transfer and/or an energy transfer takes place by induction. It is equally possible to transfer data and energy by a mechanical connection, for example by a cable or by an electrical plug connection or the like. It is thus conceivable, for example, that the first device part, that is, the filling station, for example, transfers or transmits energy wirelessly via induction or via a releasable electrical connection to the second device part which stores it in an accumulator, for example, or in a corresponding other technical apparatus for the storing of energy (capacitors).

It is conceivable that at least one of the device parts is made such that the transfer of data and energy are/is exchanged at the same time and/or by means of the same device. It is conceivable that a transponder system is particularly preferably configured such that data and energy are exchanged over the same system at the same time. This takes place wirelessly in a preferred embodiment, and preferably inductively.

Provision is made in a further embodiment of the invention that the second device part has a separate energy supply, in particular an accumulator, and/or has a separate memory for the storage of data.

It is, however, also conceivable that the second device part does not have a separate energy supply and/or that the second device part has one or more non-volatile memories for the storage of data. The second device part, which is preferably made as a mobile apparatus, can thus also be made without an internal energy supply. The dates can be stored in non-volatile memories in this embodiment.

The second device part can transmit data wirelessly, for example, via a transponder system to the first device part and/or to the third device part and also receive data wirelessly from it or them. This represents a preferred embodiment of the invention. A wired transfer is naturally also conceivable instead of or in addition to a wireless transfer.

It is thus conceivable, for example, that the second device part transfers energy wirelessly via induction or via a releasable electrical connection to the first device part and/or to the third device part.

Provision is made in an exemplary embodiment that a separate energy supply of the second device part is charged and/or that data are exchanged between a second and a third device part, with provision preferably being made that the second device part serves as a mobile wireless data store.

Provision is made in a further embodiment of the invention that the second device part has means by means of which an emergency energy supply of the first and/or third device parts takes place by means of the second device part in the event of a failure of the energy supply of the first and/or third device parts. It is thus therefore conceivable that the second device part supports the existing individual energy supply for the bridging of power failures of the first or third device parts which can be made, for example, as a filling station or as a treatment device. This can take place, for example, by a releasable electrical connection (plug-to-socket) or wirelessly via an inductive energy transfer. This situation can arise with longer term power failures. An acute situation, for example after an accident, is also conceivable, for example.

Provision is made in a further embodiment of the invention that the second device part has a memory in which treatment data relating to the treatment of the patient and/or data relating to elements inserted into the second device part and/or into the third device part, preferably disposables such as bags or other containers, filters, hose systems, treatment cassettes are storable or stored. It is thus conceivable, for example, that the second device part receives data on treatment parameters of the upcoming treatment from the third device part.

Provision is made in a further embodiment of the invention that means are provided which are made such that data stored in the second device part such as treatment data, for example, and/or data relating to inserted disposables or other components of the device parts are transmitted to the first or third device parts when brought near or coupled to them or also that a transmission of data takes place in the opposite direction. The data can then be processed further there either directly or can be forwarded, for example, via a network connection to a central control device such as a central processing unit.

It is thus conceivable, for example, that data are transferred to the first device part, which can be made as a filling station and/or emptying station, for example, on approaching the second device part and are processed further there either directly or are forwarded to a central control device (central processing unit) via the named network connection.

Provision is made in a further embodiment of the invention that test means are provided which are made such that the data transmitted by the second device part to the first or third device parts are subjected to a test. It is, for example, conceivable that the first device part, which is preferably made as a filling station, or a central control unit decides on the filling of the tank or bag (quantity and composition) into the second device part with reference to the transmitted data and, for example, passes on changed treatment parameters to the second device part as required if e.g. an expert system in the first device part or in the remote control device associated therewith arrives at different treatment parameters after evaluation of the transmitted data.

Provision is made in a further embodiment of the invention that the medical treatment arrangement has decision means which are made such that a decision is made with reference to the result of the test carried out in the test means as to whether a treatment is carried out or not. It is thus conceivable that, for example, the first device part or a preferably remote control device associated therewith refuses the filling of the second device part after evaluation of the transmitted data and thus makes a treatment impossible if it is found that, for example, an unsuitable disposable was placed in the second device part or also in the third device part.

This can be the case, for example, if, for example, a previously already used bag or disposable is used or if bags or disposables are intended to be used which are unsuitable because they are, for example, too small, incorrectly made or have otherwise unsatisfactory properties.

Provision is made in a further embodiment of the invention that disposables are inserted in the second device part and/or in the third device part which are provided with readable markings or the like.

It is not only conceivable in this manner to carry out an identification of the disposables, for instance such as to the size and the content which is to be or has been filled in, but also to detect third-party makes or the lack of features, which indicate the use of copies or third-party makes.

The first device part or a control device which is associated with it and can be arranged remotely can in this case refuse the filling and can transmit a blocking signal to the second device part which signals to the third device part that the treatment may not be started when the second device part approaches or is coupled to the third device part.

These markings can, for example, be two-dimensional matrices or RFID tags. All further suitable markings such as barcodes are also conceivable.

It is thus conceivable to provide original disposables with unforgeable markings which identify both the type and the specimen and are made known to the first device part, preferably the filling station or a remote control device associated therewith. It can thus be recognized whether original disposables are being used and whether they are unused.

Furthermore, dates of expiry can also be checked in this way to avoid the use of disposables having been stored too long. As stated, the markings can be made in a variety of forms such as a barcode, 2D, RF, etc.

A further embodiment of the present invention relates to the confusion-proof identity of the individual device parts.

It is preferred that the first device part and/or the second device part and/or the third device part has/have marks, preferably electronic labels, by means of which the respective device parts themselves and/or the belonging of a device part to another device part can be identified. It is, for example, conceivable in the initially named embodiment that the treatment station (third device part), the movable trolley (second device part) and, optionally, also the filling station (first device part) have unambiguous features, preferably via electronic labels, which are made known to the respective other device or device part. It can in this way be prevented that, for example, a filled trolley (second device part) is associated with an incorrect treatment unit (third device part).

The electronic label or also any other suitable marking can be made in a similar manner to the markings of the disposables. However, the trolley filling and treatment stations or the first, second and/or third device parts preferably also transmit individual identification codes by which an unambiguous association is possible in the wired communication.

It is possible in this manner that those device parts cooperate for which this is also provided.

Provision is made in a further embodiment that the first device part and/or the second device part and/or the third device part has/have one or more indication and/or input devices, in particular displays. No restrictions are present with respect to the type of the displays. The can, for example, be TFT (LCD), OLED or e-paper displays.

It is thus conceivable, for example, that the second device part, in particular a movable trolley for the purpose of information indication, is provided with a display and/or with other optical, acoustic or haptic signal displays. This applies accordingly to the other device parts.

The signal indications or displays can, as stated, include all types of displays. Input apparatus, such as a keyboard or a touch screen, can furthermore be provided. It is conceivable in this respect that the touch screen and the display device are formed by one and the same component.

If it is an electronic display (e-paper), this provides the advantage that a trolley or the second device part can also be made without an internal energy store since the indication of the display is also maintained without a power supply. The operator can thus also read off the information when the trolley or the second device part is not located in the first or third device parts, that is, in accordance with a preferred embodiment, not in the filling station unit and/or in the treatment unit.

The data and/or energy transmission in accordance with the invention preferably takes place inductively in accordance with known processes. For this purpose, the transmitter has a transmission coil which emits a magnetic alternating field. The receiver can have a reception coil in which an electric alternating voltage is induced if it is in the field of the transmission coil. This AC voltage is rectified at the receiver and, dependent on the embodiment, the resulting electrical energy is preferably stored in a rechargeable battery.

The data transmission can take place in a variety of ways in this respect. There can be named by way of example, but not restrictively: frequency modulation, phase modulation, amplitude modulation, frequency pulses. The arrangement of transmission/reception coil is preferably operated by addition of components compensated for idle power (capacitors) in resonance with the transmission frequency to ensure an energy transmission which is as good as possible. Modulation types are therefore preferred in the energy transmission which do not change the frequency of the transmission signal (phase modulation, frequency pulses).

The data transmission from the receiver to the transmitter can take place in a known manner by load modulation. In this respect, the transmission power is primarily modulated at the reception side by addition of a load resistance corresponding to the data content.

As initially stated, the medical treatment arrangement is not restricted to a blood treatment such as to a dialysis treatment, although such a treatment represents a preferred application area of the medical treatment arrangement in accordance with the invention. The use as a dialysis machine, for hemodialysis, peritoneal dialysis, etc. is, for example conceivable, but also for other medical treatments.

Further details and advantages of the present invention will be explained in more detail with reference to an embodiment shown in the drawing.

The embodiments relate to three variants of the treatment arrangement in accordance with the invention, with the disposable being made with a 2D matrix in the first variant (FIG. 1 to FIG. 16) and the communication between the filling station and the trolley and between the trolley and the treatment unit taking place by inductive coupling.

In the second variant in accordance with FIGS. 17 to 29, the bag has an RFID tag and the communication between the filling station and the trolley and between the trolley and the treatment unit takes place magneto-inductively.

In the third variant in accordance with FIGS. 30 to 43, the bag has a 2D matrix and the communication between the filling station and the trolley and between the trolley and the treatment unit takes place by means of RFID.

There are shown:

FIGS. 1 to 16: the data and energy transfer between the trolley, the filling station and the treatment device in a first embodiment;

FIGS. 17 to 29: the data and energy transfer between the trolley, the filling station and the treatment device in a second embodiment; and FIGS. 30 to 43: the data and energy transfer between the trolley, the filling station and the treatment device in a third embodiment.

FIG. 1 shows a component of the medical treatment arrangement designated as a first device part with the reference numeral 10 in an embodiment of the invention. It is a filling station and an emptying station for the filling and emptying of a mobile trolley 20 which serves as a second device part. The third device part is shown with the reference numeral 30 and is made in the embodiment shown here as a dialyzer for the carrying out of a dialysis treatment.

A bag 21 is located in the trolley 20 and is made with a 2D label 22 so that the bag type and the bag contents are clearly identifiable. In the embodiment shown here, a data transmission thus takes place from the bag to the filling station via a 2D matrix.

As soon as the trolley 20 has been introduced into the filling station 10 or has approached it, a reading and/or writing process takes place, and indeed unidirectionally or also bidirectionally between the trolley 20 and the filling station 10. Apart from this, a charging process can also occur, for example of an accumulator of the trolley 20 by the filling station 10.

The trolley 20 can have, in addition to an energy store, a data store and/or an electronic system for the evaluation of data.

The energy store can be charged inductively, for example, by the filling station 10 and also by the treatment device 30. It is also conceivable that energy is transferred from the energy store of the trolley 20 to the filling station 10 and/or to the treatment device 30.

These aforesaid processes can take place by inductive coupling or magnetoinductively.

The same applies accordingly to the communication or to the energy exchange between the trolley 20 and the treatment device 30, as is likewise indicated in FIG. 1.

The filling station 10 and the treatment device 30 can preferably be made as immobile or substantially immobile and are in any case intended for a fixed-position use. The case is, however, generally also covered by the invention that these units are also movable, as also applies to the trolley 20.

FIG. 2 shows the bag 21 of the trolley 20 in an enlarged representation, said bag having the task of receiving fresh dialysis solutions from the filling station 10 and of dispensing the solution to the treatment device 30 or of making it available to it after its movement to the treatment device 30. The object can further compromise receiving consumed dialysis fluid from the treatment device 30 and of dispensing it to the filling station 10 again after the moving to the filling station 10.

The term "filling station" must therefore be given a wide interpretation. It can relate both to the filling process and to the emptying process.

A breakable bag pin is marked by the reference numeral 230 in accordance with FIG. 2. This pin is broken for the first time by a corresponding apparatus in the treatment device 30 on insertion into the treatment device 30 and thus marks a used bag. A bag marked in this way is recognized (e.g. optically or mechanically) by a corresponding sensor on reinsertion into the filling station and a refilling is prevented. A re-use is reliably prevented in this way.

In a further alternative or additionally conceivable embodiment, the measurement of the conductivity of the bag contents is provided. Concentrates can be stored in the unused bag which are dissolved in the filling station 10 on the filling with RO water. A solution is thus set with a characteristic conductivity which changes by mass transfer by the use in the treatment device 30, for example during a dialysis treatment. The filling station 10 checks the conductivity of the filled bag and recognizes, if the bag was not emptied in the filling station 10 after a prior use and is provided for re-use in a prohibited manner, that no concentrates which characteristically change the conductivity were present in the bag. A conclusion on re-use is thus made and further measures can be taken to prevent the treatment with this re-used bag. Such measures are, for example, the emptying in the filling station 10, the generation of a warning signal or of another alarm signal, the marking of the bag, etc.

FIG. 3 shows an overview image substantially corresponding to FIG. 1 of the components of the medical treatment arrangement in accordance with the invention, with it being clarified here that both the data transfer and the transfer of energy take place magnetoinductively in the embodiment shown here.

FIG. 4 shows the step of the equipping of the trolley 20 with a new bag 21. As can be seen from FIG. 5, the trolley 20 is then connected to the filling station 10, and indeed such that a fluid transfer and, optionally, a data transfer and/or an energy transfer is possible.

FIG. 6 shows that the bag data and the trolley data are read and FIG. 7 shows the state that the bag was now filled and the data, in particular the data for the filling of the bag, are also simultaneously being transferred to the trolley 20. In the example shown, the information is transmitted to the trolley 20 that its tank or bag is filled and contains unused dialysis solution.

The data transmitted between the device parts of the present invention can generally be any desired information, for example treatment data, patient data, device data, device component data, etc. It is, for example, conceivable that the transmitted information relates to the composition of the concentrates or of the finished solution.

FIG. 8 shows the state in which the connection between the trolley 20 and the filling station 10 was separated.

Provision is made in a preferred embodiment of the invention that the trolley 20 has a display in which the data for the user are visibly shown which are stored in a memory unit of the trolley. This display can, for example, be an e-paper, which brings along the advantage that a reading of the data is also possible when the trolley 20 does not have its own energy supply.

The trolley 20 filled by means of the filling station 10 or the filled tank or bag of the trolley 20 is then moved with the trolley 20 to the treatment device 30 and connected to it, as can be seen from FIG. 9.

As can further be seen from FIG. 10, the trolley data are then read out and data are likewise transferred to the trolley. Provided that the data read out from the trolley 20 are in order, the treatment is released.

In the example shown, the trolley 20 carries the information, after the end of the treatment, that the bag is full and is used.

FIG. 11 characterizes the end of the treatment and the separation of the connection between the trolley 20 and the treatment device 30.

The container of the trolley 20 filled with the used dialysis fluid is then moved with the trolley 20 to the filling station 10 which serves the emptying of the tank in this case (cf. FIG. 12).

In this respect, the display of the trolley 20 shows the data which were stored on the trolley. In this respect, for example, it can be the data which were transferred from the treatment device 30 to the trolley 20.

FIG. 13 shows the state in which the trolley data are read out of the filling station 10. Subsequently, in accordance with FIG. 14, the bag of the trolley 20 is emptied by the filling station 10.

FIG. 15 shows the state that the bag was emptied and these corresponding data are also immediately transferred to the trolley 20. In this case, it is the information that the bag is empty and used.

Subsequently, in accordance with FIG. 16, a bag change follows in that the used bag in accordance with step 1 is replaced by a new bag in accordance with step 2.

FIGS. 17 to 29 show a further embodiment which only differs from the first embodiment in accordance with FIGS. 1 to 16 in that the bag is not made with a 2D matrix as a characterization means, but with an RFID tag which can be read and written. In another respect, reference is made accordingly to the above statements on the first embodiment.

In this embodiment, the communication between the filling station and the trolley and also between the trolley and the treatment unit takes place magnetoinductively, as can be seen from FIG. 17.

FIG. 18 shows the step of equipping the trolley 20 with the new bag 21 which has an RFID tag 23 as the communication means.

FIG. 19 shows the step of connecting the trolley 20, into which the bag 21 is inserted, to the filling station 10.

In accordance with FIG. 19a, the bag data of the bag of the trolley 20 are then read out by the filling station 10. In this case, it is the bag identification and the information that the bag is empty and unused.

The bag is then filled by the filling station 10 in accordance with FIG. 20 and the corresponding data are simultaneously transferred to the RFID tag of the bag.

In accordance with FIG. 21, the connection between the trolley 20 and the filling station 10 is then separated and the display of the trolley 20 shows the data or at least some of the data which are stored in the RFID tag of the bag.

FIG. 22 shows the connection of the trolley with filled tank with the treatment device 20.

FIG. 23 relates to the release of the treatment. For this purpose, the bag data are read out and the data present after the carrying out of the treatment are transferred from the treatment device 30 to the RFID tag of the bag.

FIG. 24 characterizes the end of the treatment and the connection between the trolley 20 and the treatment device 30 is separated.

The trolley 20 filled with the used dialysis solution is then moved to the filling station 10 (cf. FIG. 25). The trolley 20 shows the data in its display which are stored on the RFID tag.

As in the first embodiment, the bag change in accordance with steps 1 and 2 follows this, with the used bag 1 being replaced by a fresh bag 2 in accordance with step 1.

FIGS. 30 to 43 show a third embodiment of the present invention in which the bag has a 2D matrix for its identification and the communication takes place via RFID between the filling station and the trolley and between the trolley and the treatment unit.

In contrast to the two first embodiments, provision is made in the third embodiment that the trolley 20 does not have its own energy store in this embodiment and the display of stored data takes place via an e-paper display. A use of a trolley with its own energy store is, however, generally also conceivable in this embodiment. Energy is needed once for the writing of an e-paper and for the writing/reading of non-volatile memories (e.g. EEPROM). Once the process of the state change of the display or of the memory or memories is ended, no further energy is required to keep the state stable. It is essential for the third embodiment that the trolley 20 in this embodiment does not have its own energy store.

The trolley 20 in this embodiment is made with an RFID tag 24 which is readable and writable. Data of the RFID tag can be shown on the display of the trolley 20.

Figure 30:
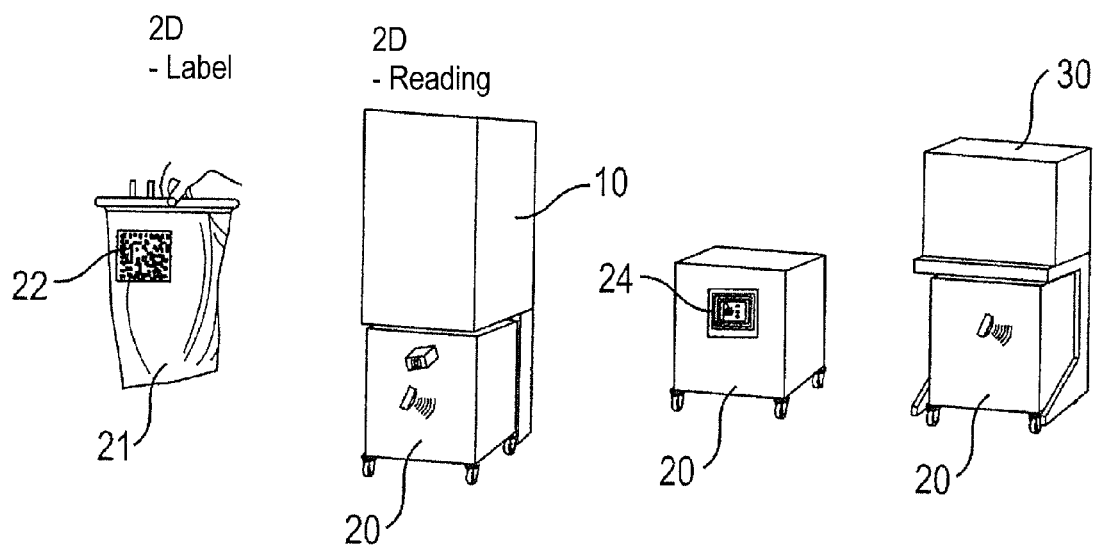

It results from FIG. 30 that RFID is used as the communication medium for the communication between the filling station and the trolley and between the trolley and the treatment unit and that the bag 21 itself is made with a 2D label or with a 2D matrix.

Figure 1:
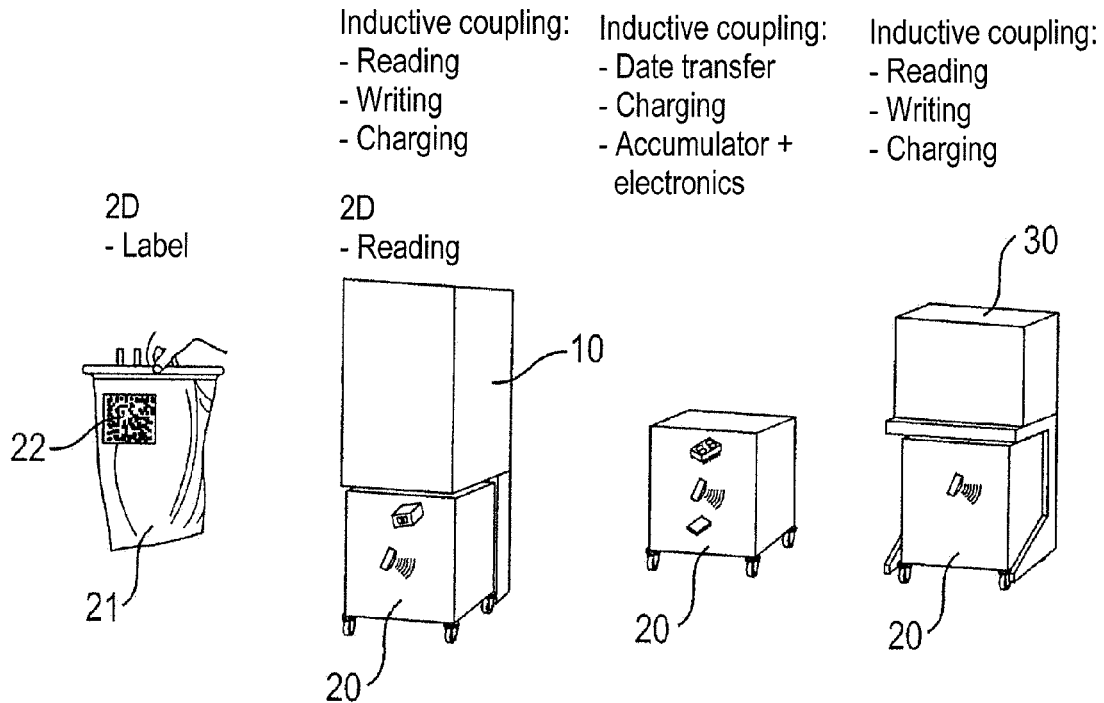
Figure 2:
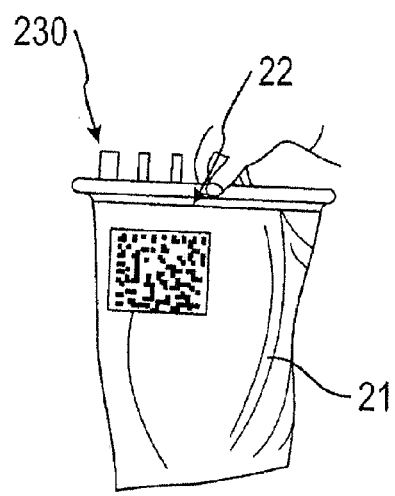
Figure 3:
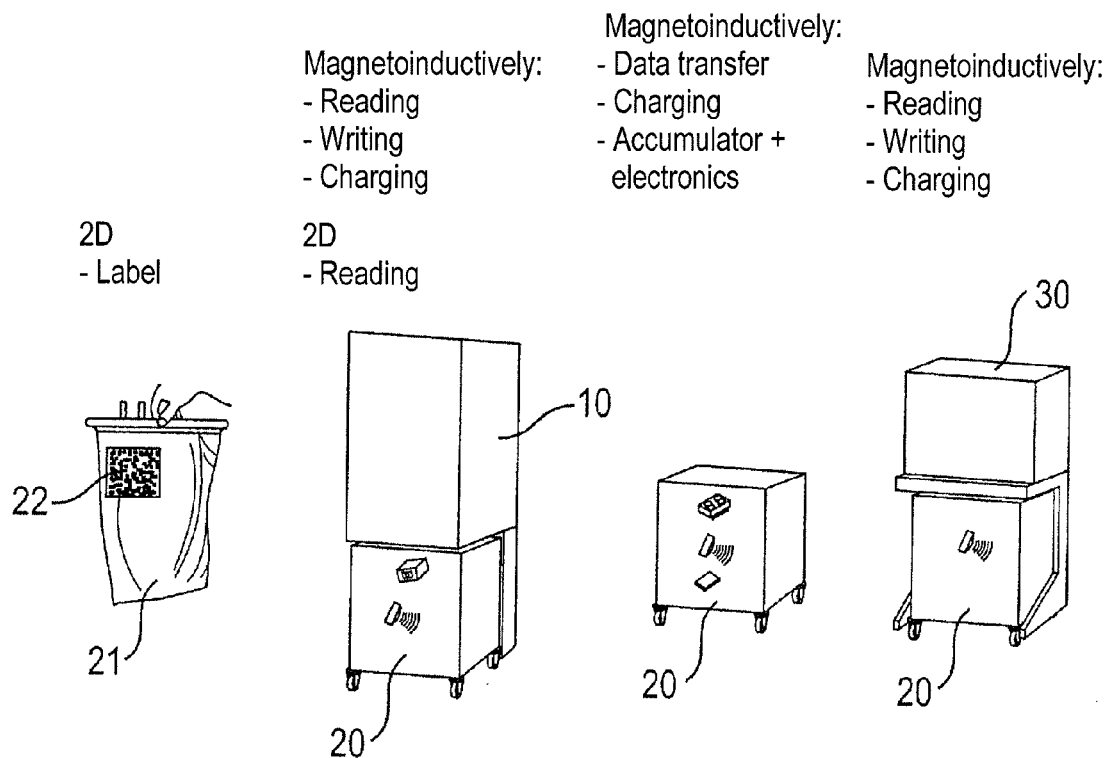
Figure 4:
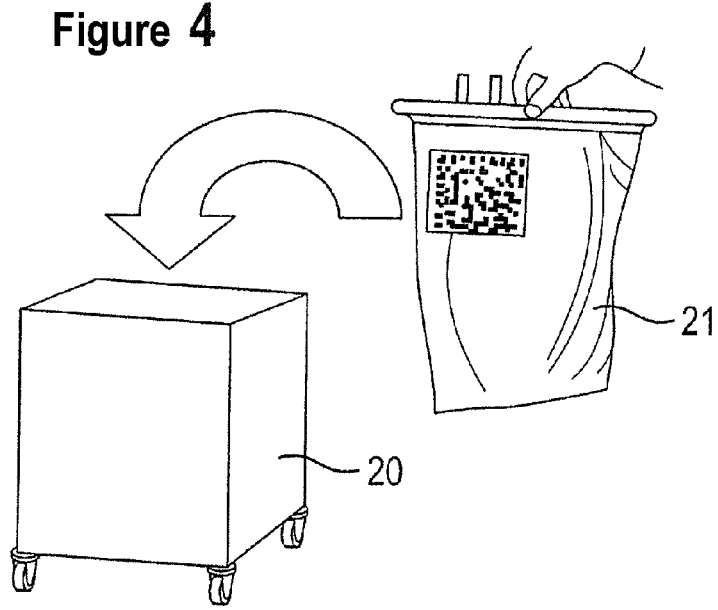
Figure 5:
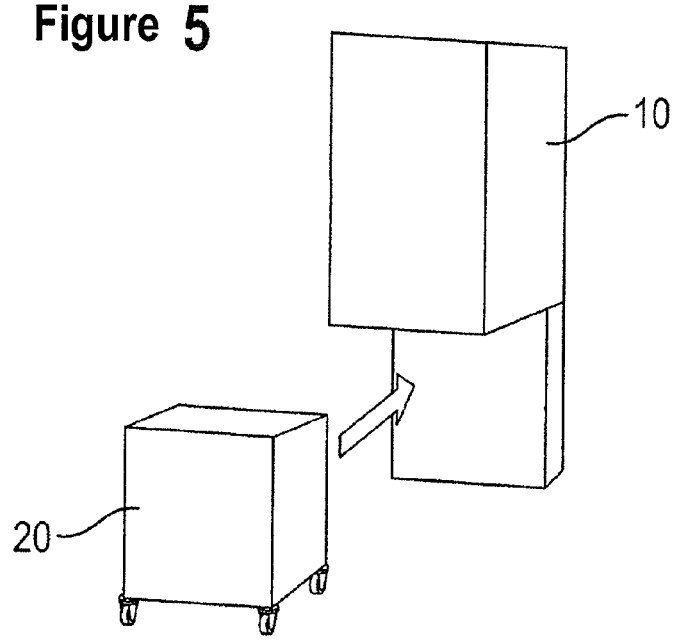
Figure 6:
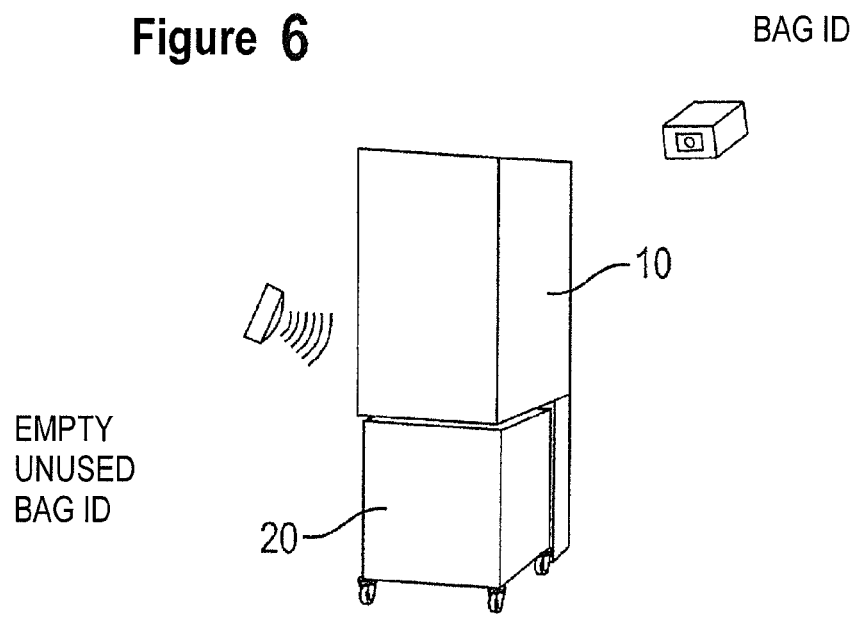
Figure 7:
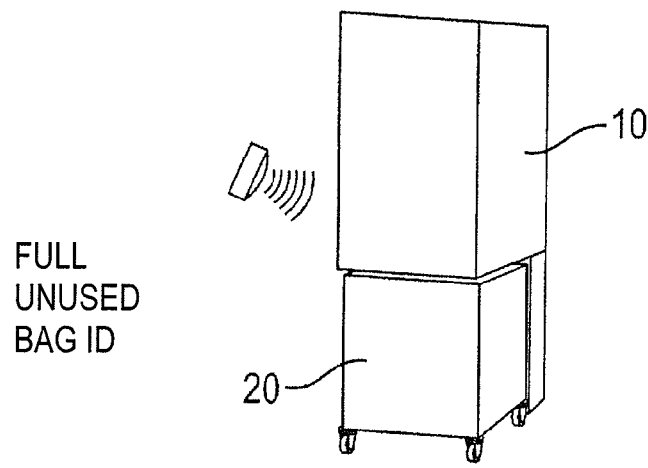
Figure 8:
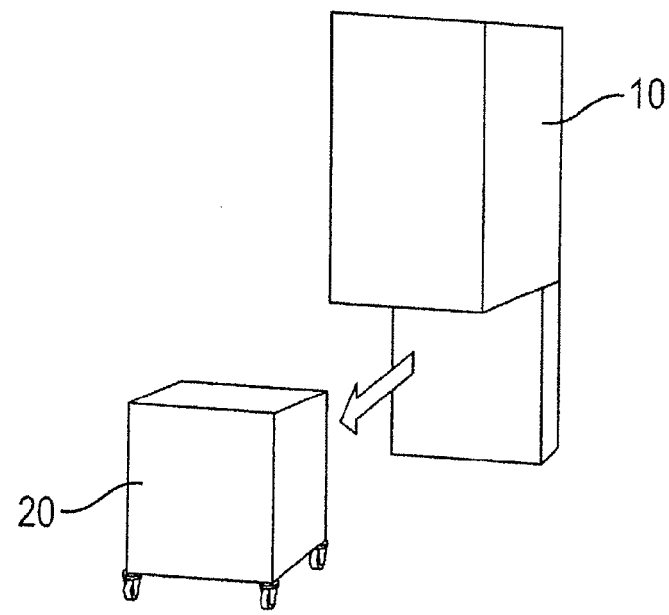
Figure 9:
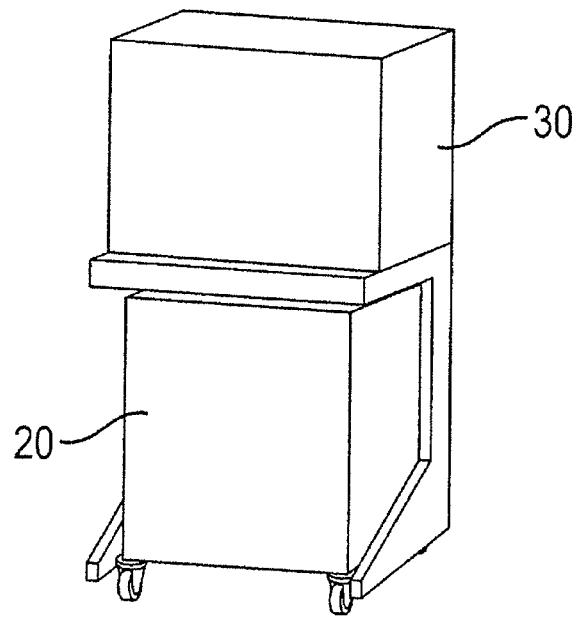
Figure 10:
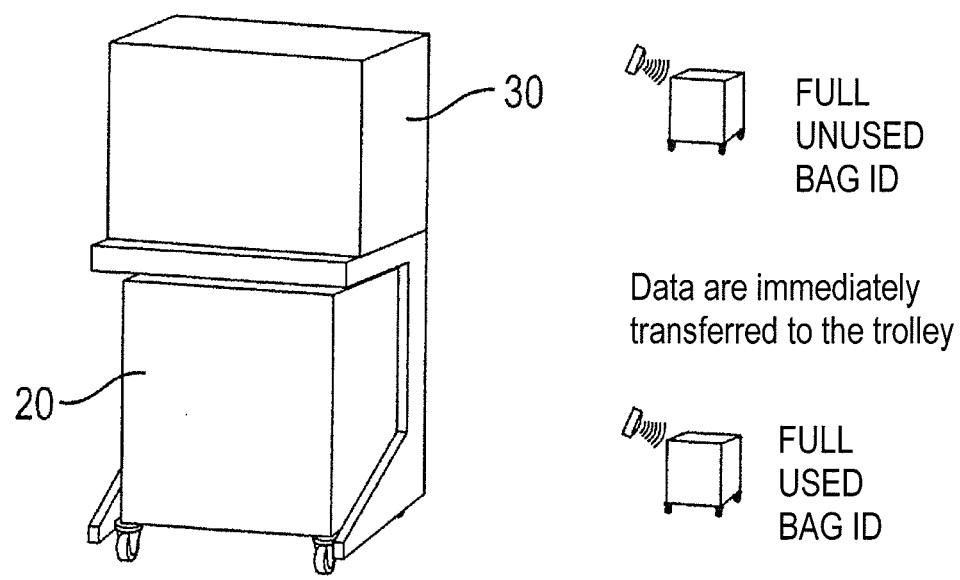
Figure 11:
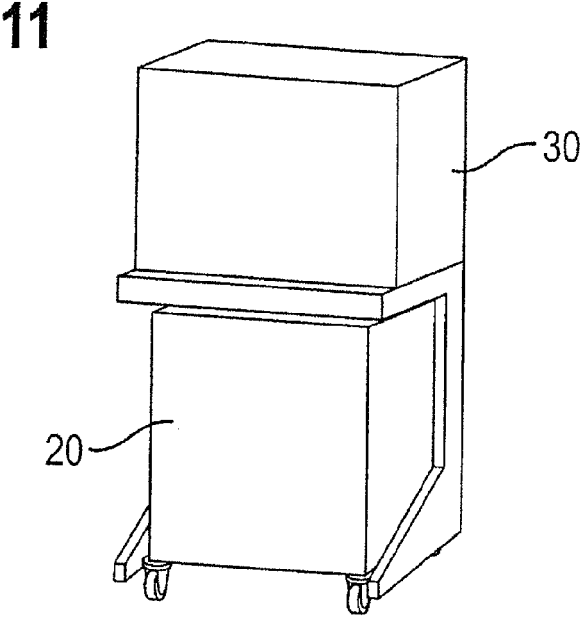
Figure 12:
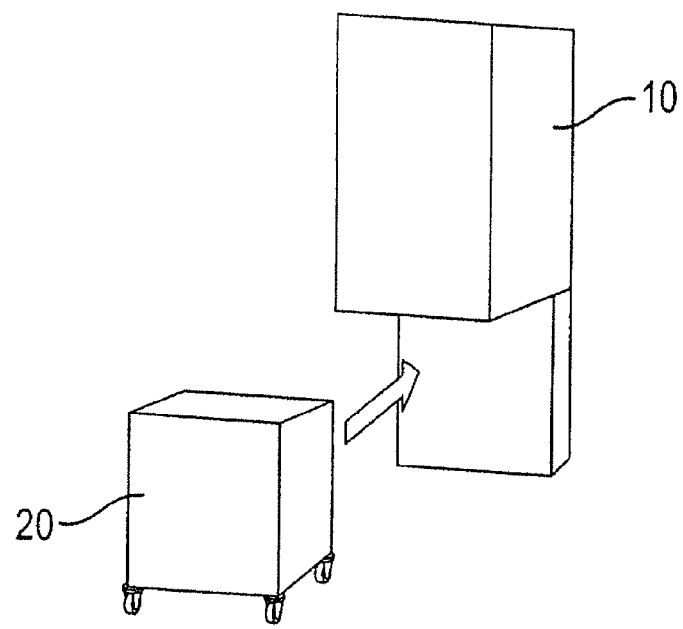
Figure 13:
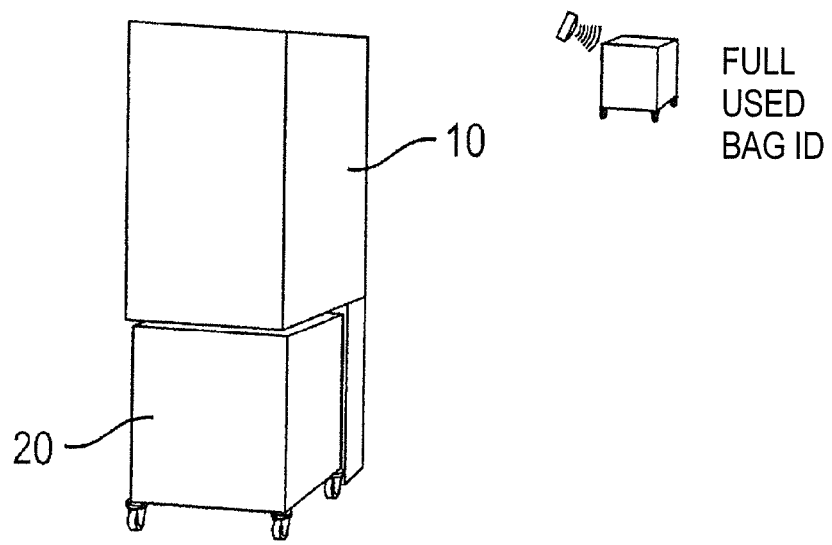
Figure 14:
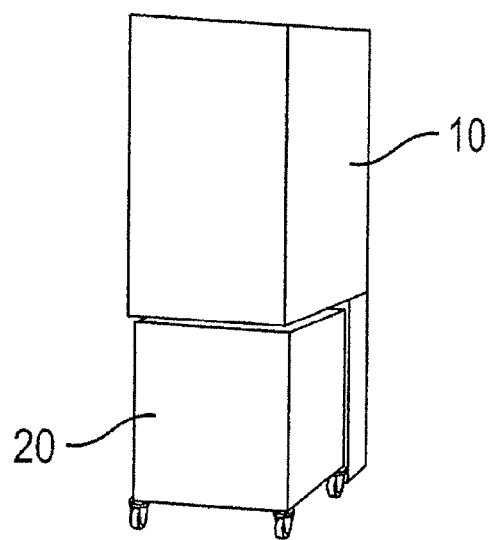
Figure 15:
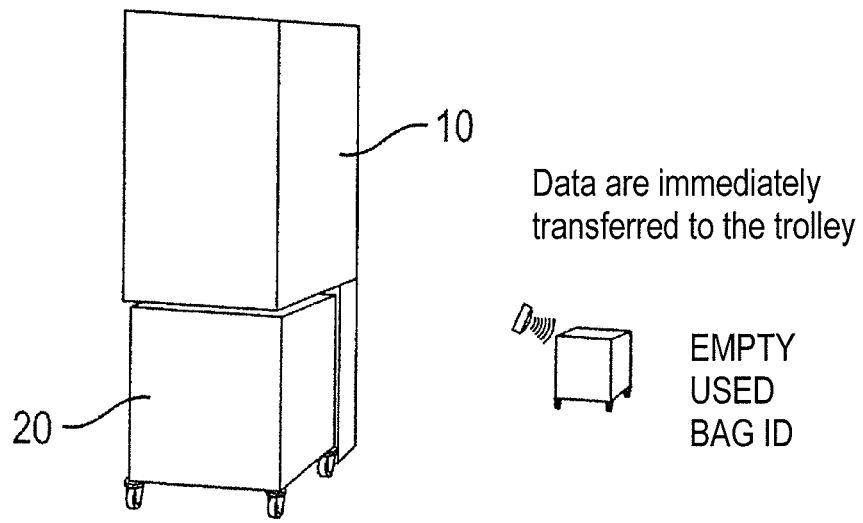
Figure 16:
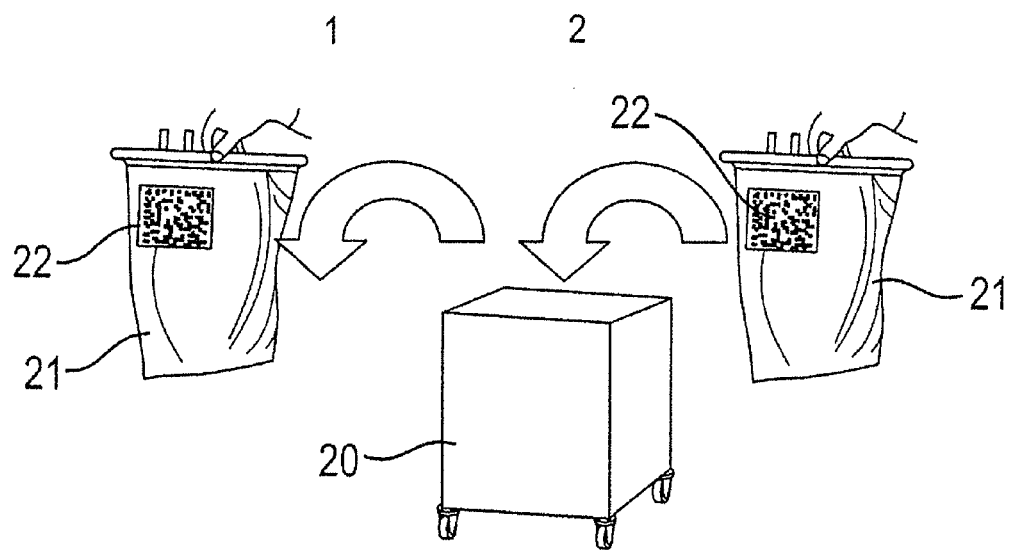
Figure 17:
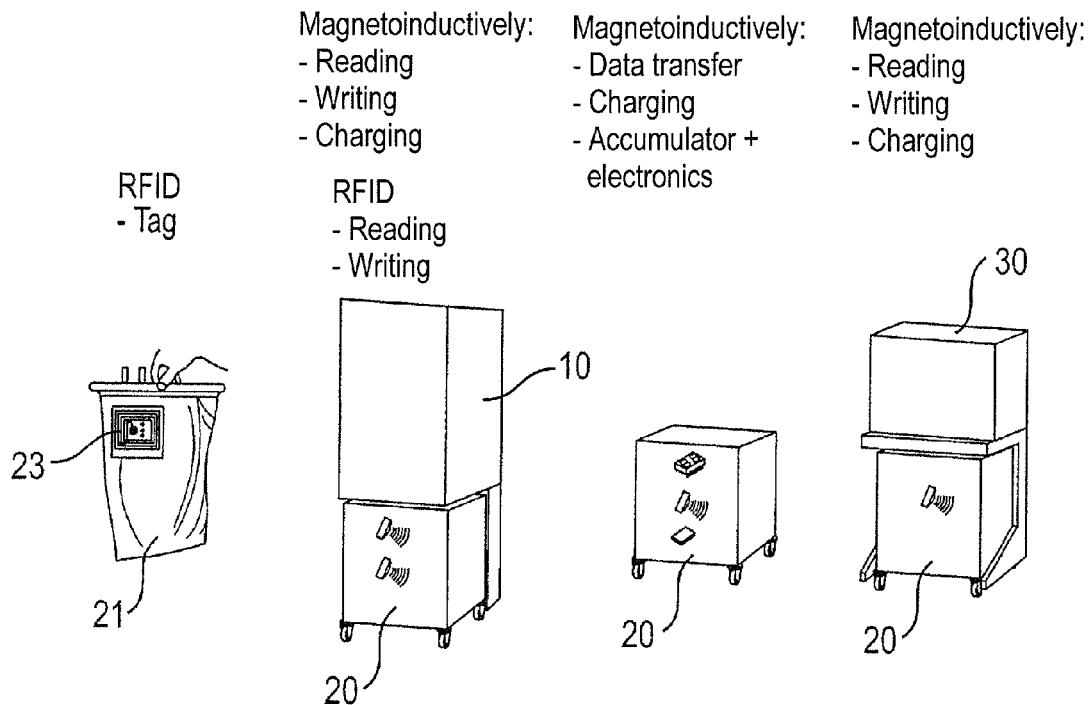
Figure 18:
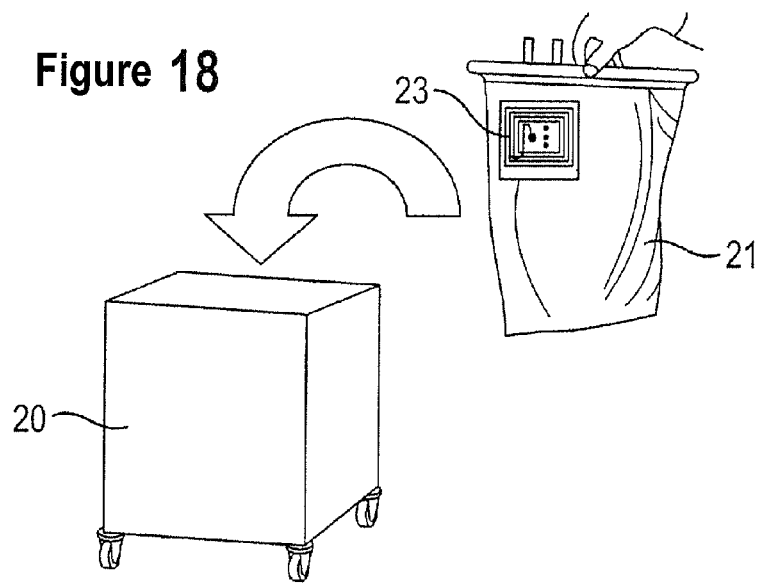
Figure 19:
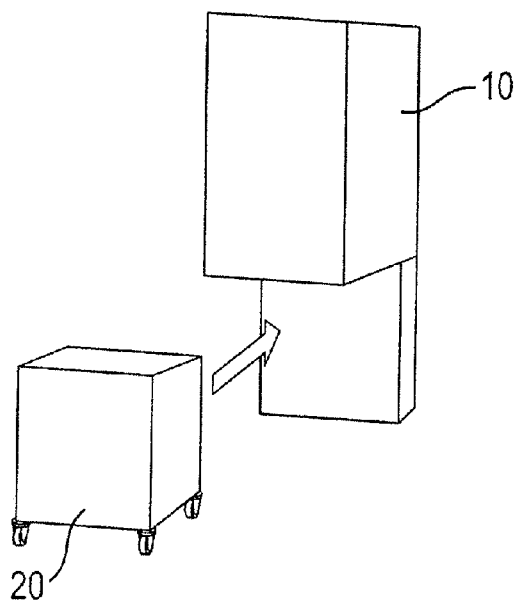
Figure 19A:
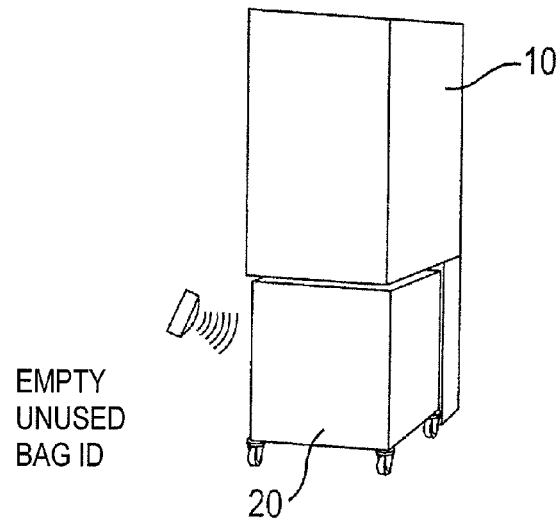
Figure 20:
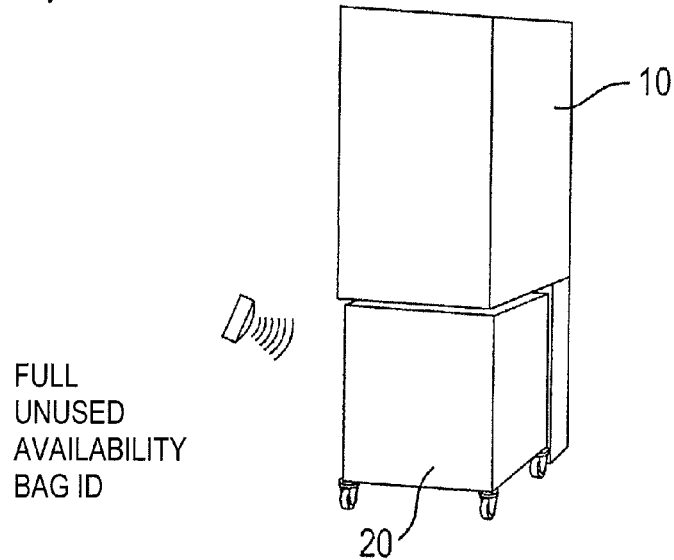
Figure 21:
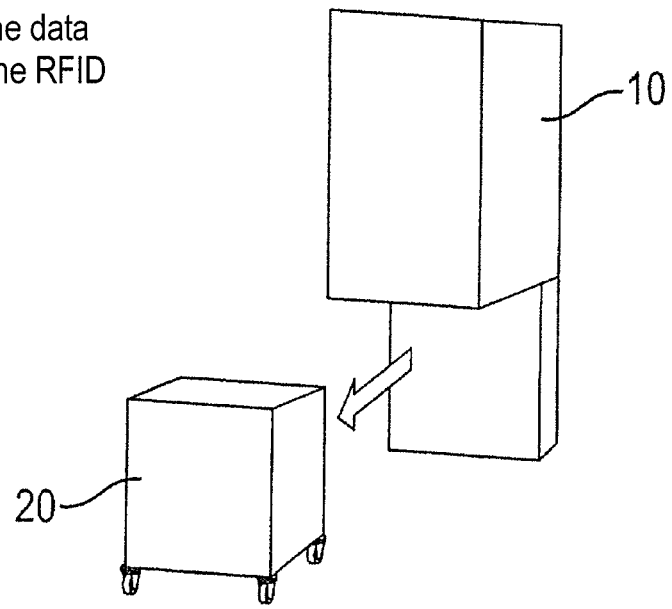
Figure 22:
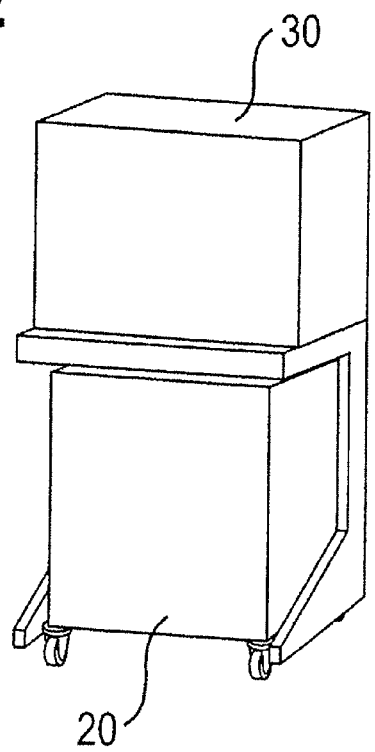
Figure 23:
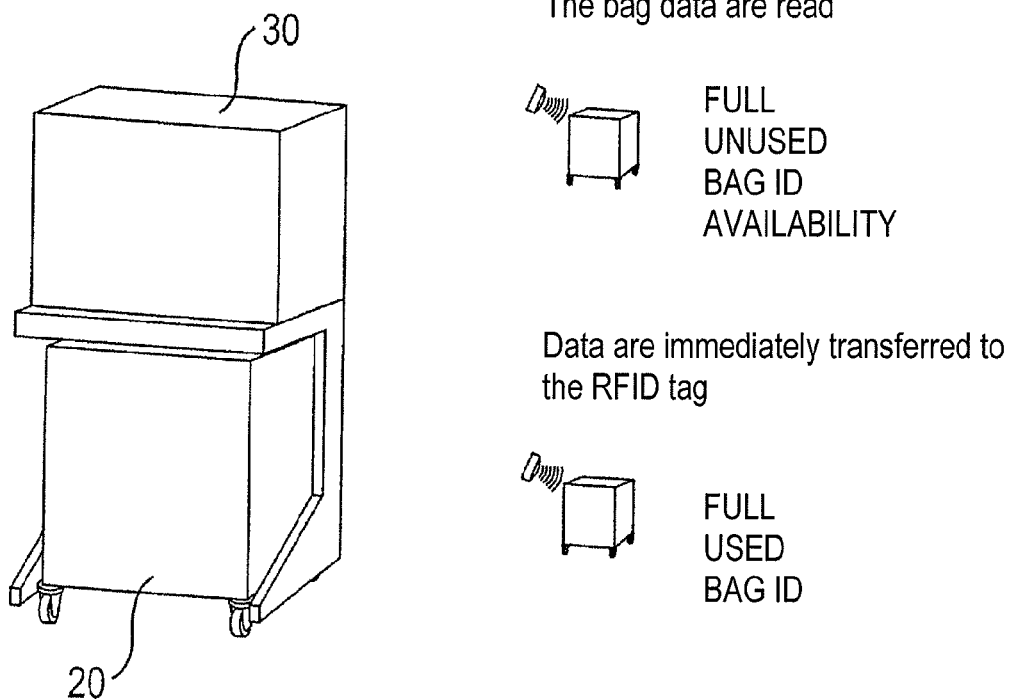
Figure 24:
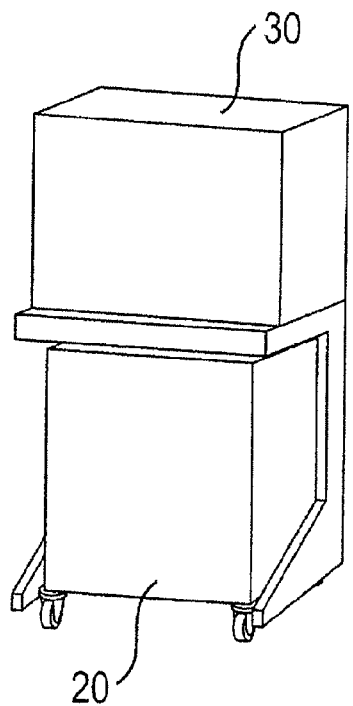
Figure 25:
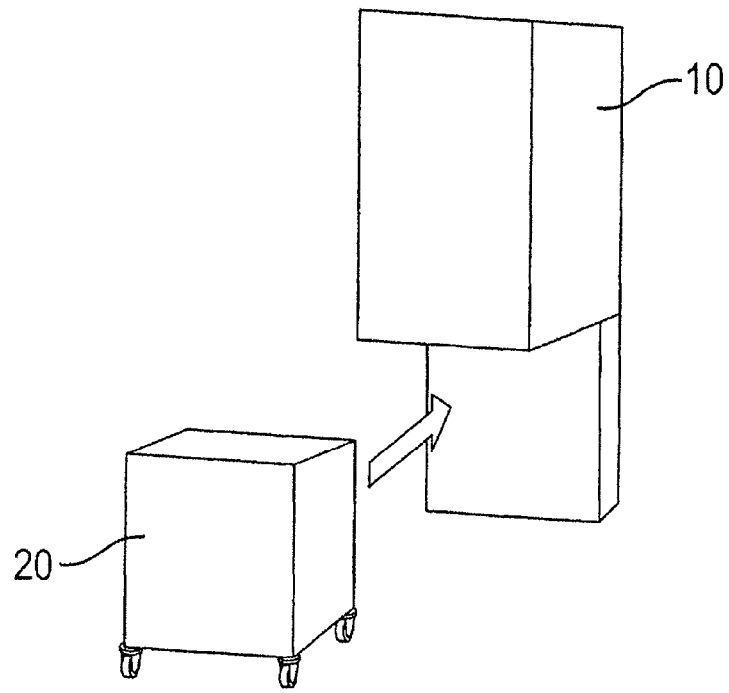
Figure 26:
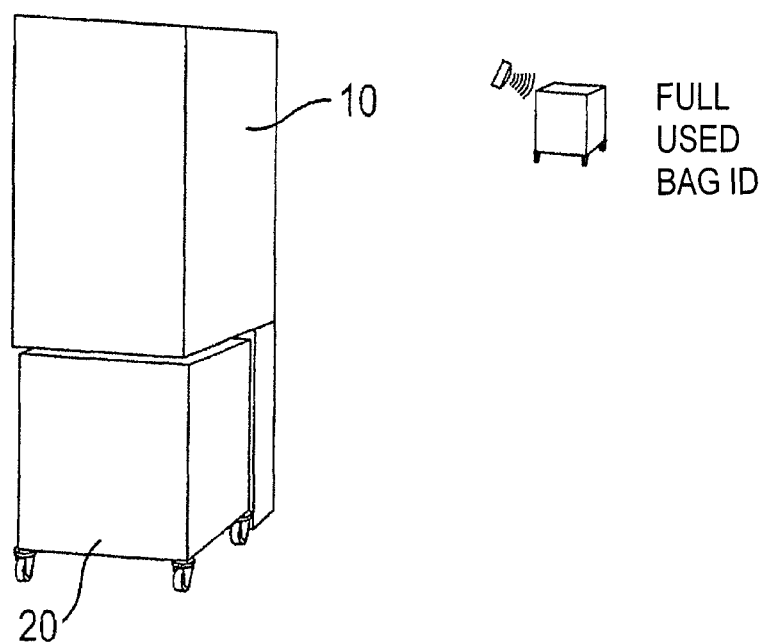
FIG. 26 shows the readout of the bag data by the filling station 10 and FIG. 27 shows the process of the bag emptying by the filling station 10.
Figure 27:
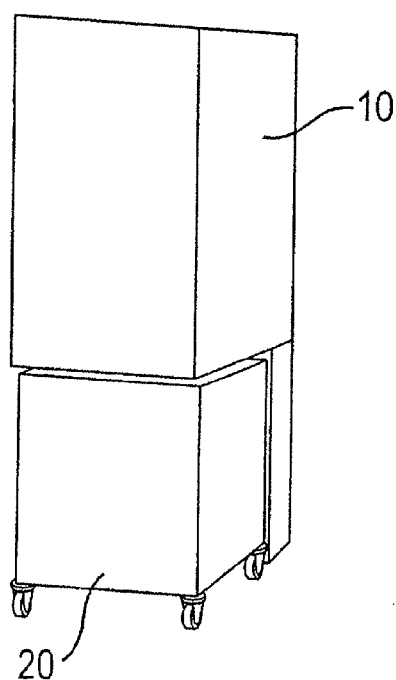
Figure 28:
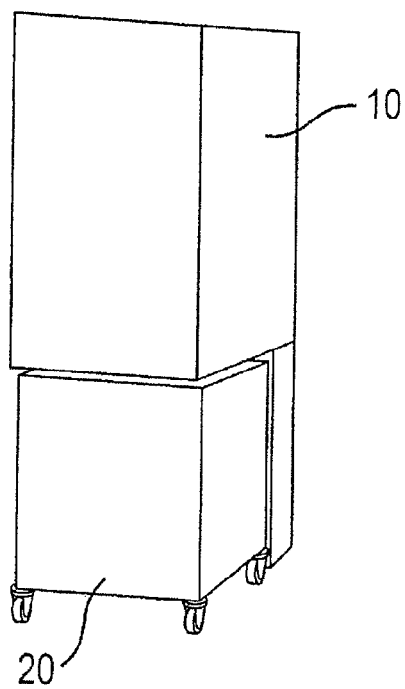
FIG. 28 shows a state in which the bag was emptied and the data are simultaneously transferred to the bag RFID tag.
Figure 28:
Figure 29:
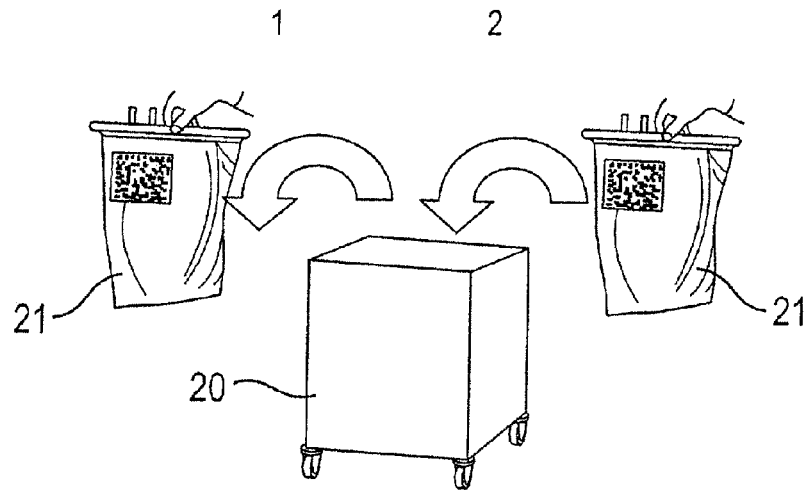

Otherwise, the device parts correspond to the embodiment in accordance with FIG. 1 so that reference is made accordingly.

Figure 31:
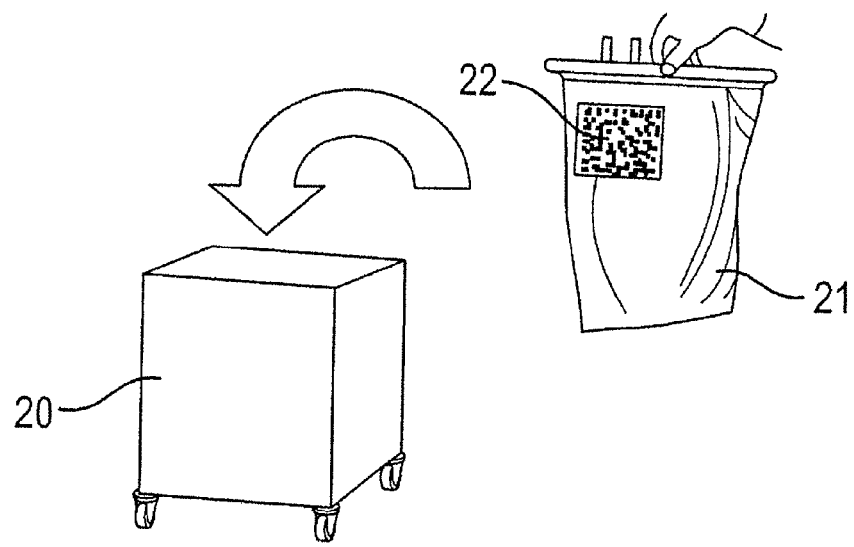
Figure 32:
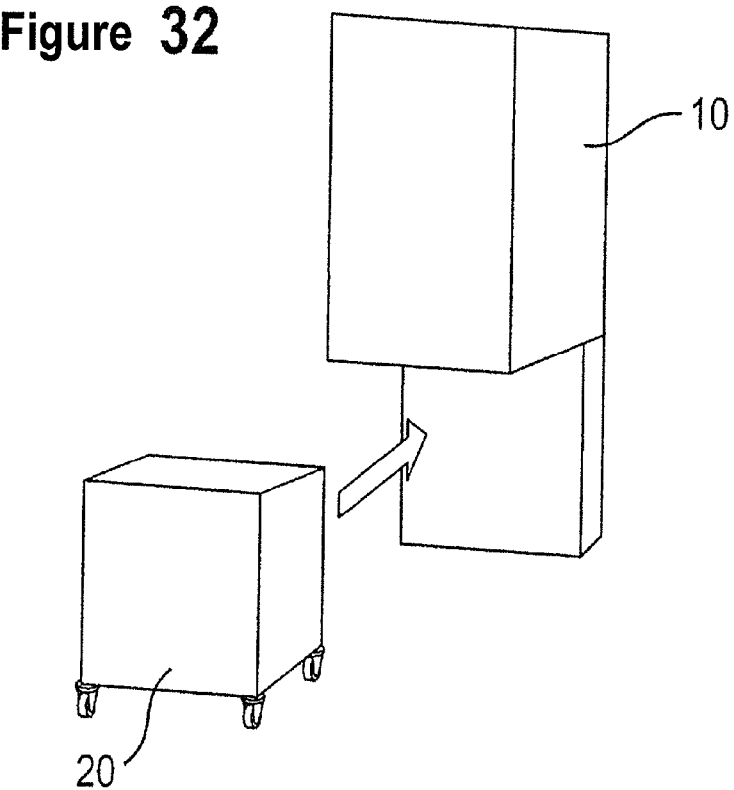
Figure 33:
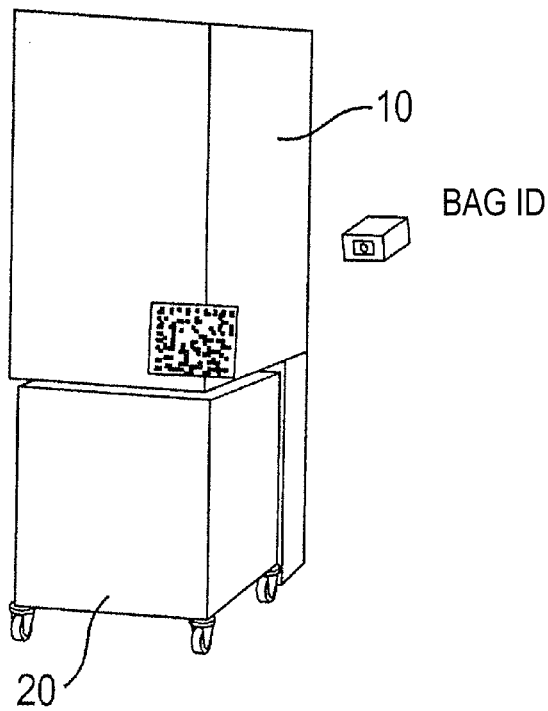

FIG. 31 shows the equipping of the trolley 20 with a new bag 21; FIG. 32 shows the connection to the filling station 10; and FIG. 33 shows the reading out of the bag data of the 2D label by the filling station 10.

Figure 34:
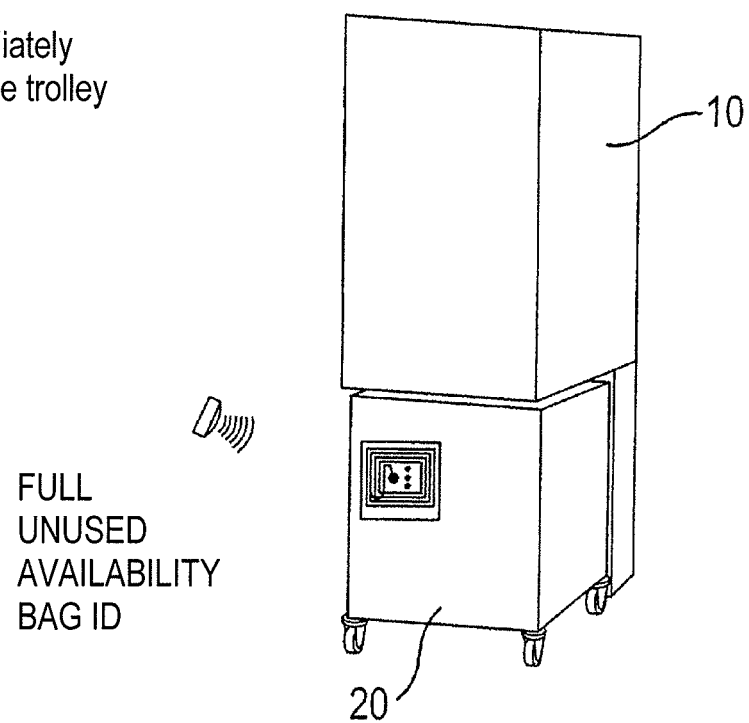

FIG. 34 shows the filling of the bag of the trolley 20 by the filling station 10. In this respect, data are simultaneously transferred to the trolley 20 or to its memory.

Figure 35:
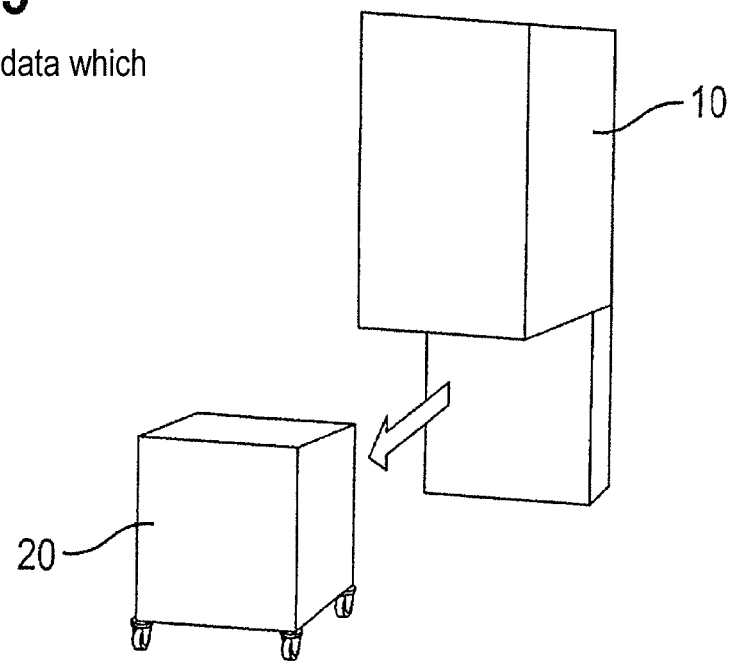

In accordance with FIG. 35, the connection is then separated and the trolley shows the data stored in the trolley 20 on a display made as e-paper.

Figure 36:
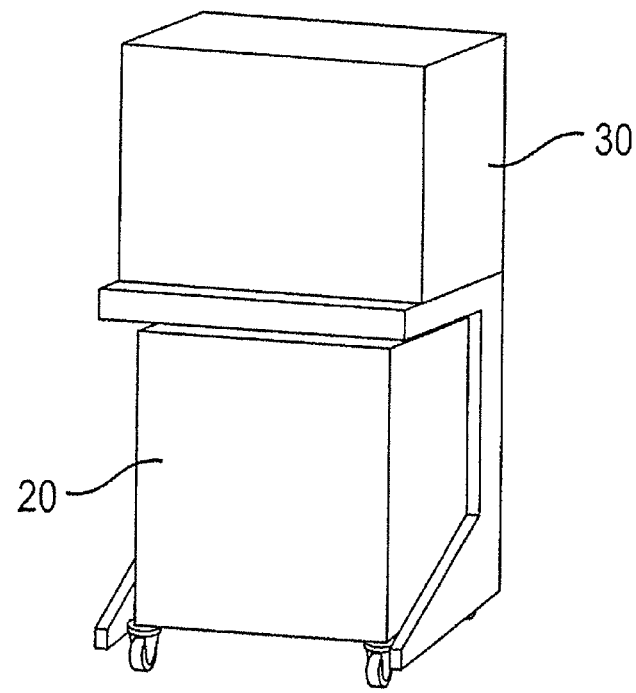
Figure 37:
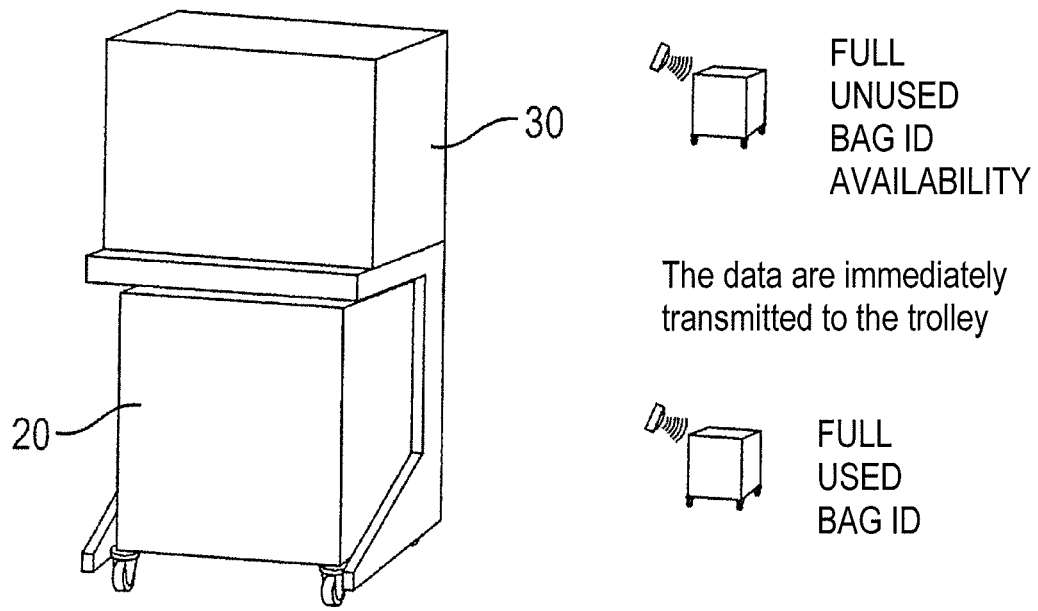

The trolley 20 is subsequently moved to the treatment device 30 and connected to it, as can be seen from FIG. 36.

If the trolley data are in order, the treatment is released. The data relating to the treatment are then transferred to the trolley immediately after the treatment, as can be seen from FIG. 37.

Figure 38:
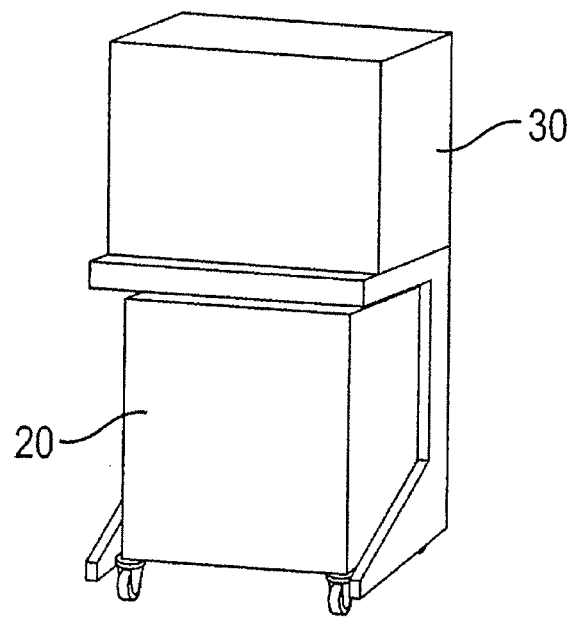

FIG. 38 characterizes the end of the treatment. The connection between the treatment device 30 and the trolley 20 is separated.

Figure 39:
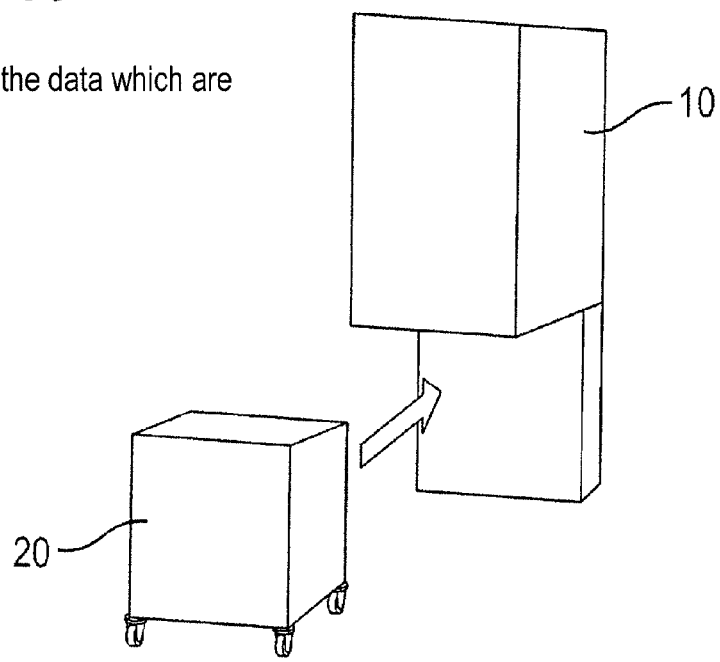

FIG. 39 relates to the connection of the trolley 20 to the filling station 10. The display here also shows the data which are now stored in the trolley 20.

Figure 40:
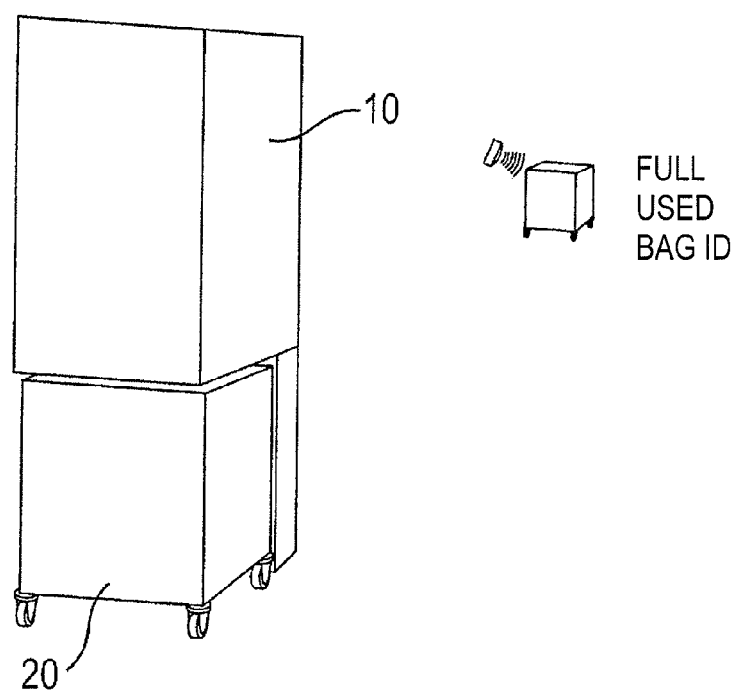
Figure 41:
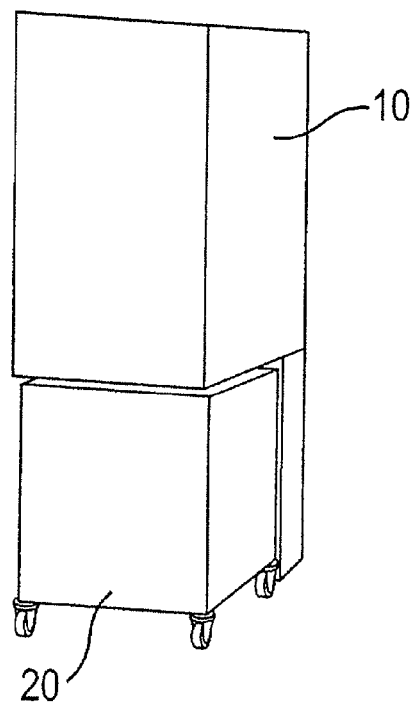

In accordance with FIG. 40, the trolley data are then read out by means of the filling station 10 and the bag is emptied in accordance with FIG. 41.

Figure 42:
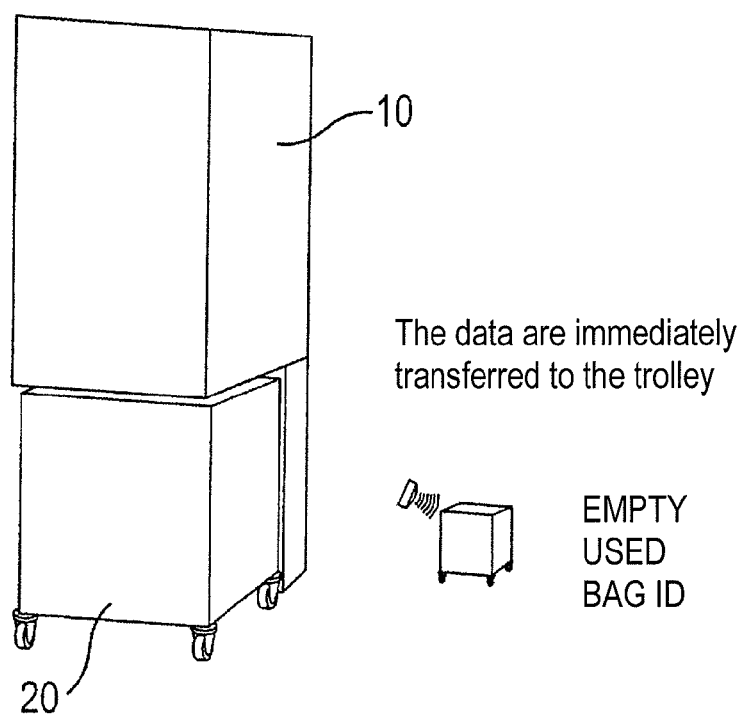
Figure 43:
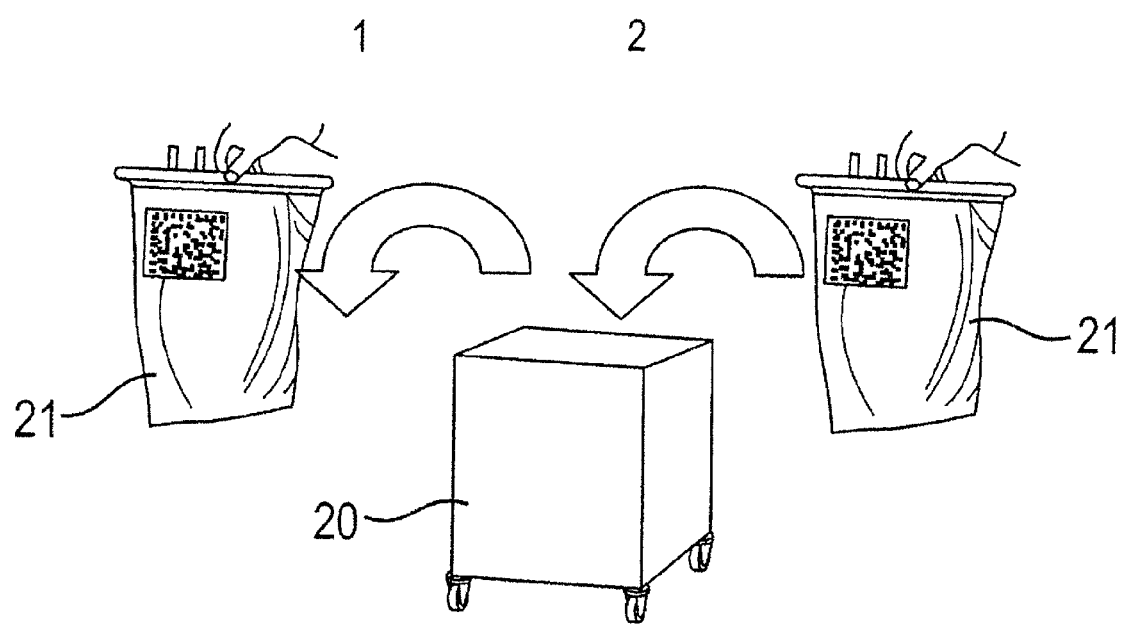

The corresponding data are then immediately transferred to the trolley 20 in accordance with FIG. 42 after the emptying of the tank or of the bag of the trolley, as soon as the bag was emptied. In accordance with FIG. 43 this is followed by the bag change as also in the preceding embodiments. A consumed bag is replaced in accordance with step 1 by a fresh bag in accordance with step 2 and the trolley is again available for filling in a filling station.

The invention claimed is:

1. A medical treatment arrangement comprising
    a) at least one filling device,
    b) at least one treatment device, and
    c) at least one mobile container device reversibly connectable, and movable with respect, to each of the filling and treatment devices,
    wherein the mobile container and treatment devices are configured to carry out only when connected together the complete medical treatment of a patient,
    wherein each of the devices has an energy transfer part configured to unidirectionally or bidirectionally transfer energy to another device sufficient to power, or charge a power supply carried by, the other device,
    wherein each of the devices has a data transfer part configured to unidirectionally or bidirectionally transfer data between the mobile device and the filling and treatment devices,
    wherein the energy transfer part and the data transfer part are configured to transfer energy and data simultaneously, and
    wherein one of the devices has a power supply for another of the devices.

2. The medical treatment arrangement according to claim 1, wherein at least one of the filling and treatment devices is immobile or substantially immobile.

3. The medical treatment arrangement according to claim 1, wherein the filling and mobile container devices are configured to carry out a medical blood treatment of a patient.

4. The medical treatment arrangement according to claim 3, wherein the medical blood treatment is a dialysis.

5. The medical treatment arrangement according to claim 1, wherein at least one of the energy transfer parts transfers energy in a wireless manner.

6. The medical treatment arrangement in accordance with claim 1, wherein each of the energy transfer parts transfers energy in a wireless manner.

7. The medical treatment arrangement in accordance with claim 1, wherein at least one of the energy transfer parts transfers energy in a wireless manner by induction.

8. The medical treatment arrangement in accordance with claim 1, wherein the mobile container device has the power supply for another device.

9. The medical treatment arrangement in accordance with claim 1, wherein the mobile container device does not have the power supply for another device.

10. The medical treatment arrangement in accordance with claim 1, wherein the mobile container device has the power supply as an emergency energy supply for at least one of the filling and treatment devices triggered by failure of energy supply of the filling or treatment device.

11. The medical treatment arrangement according to claim 1, wherein the mobile container device has a memory configured to store at least one of patient treatment data and data relating to elements inserted into at least one of the filling and treatment devices.

12. The medical treatment arrangement according to claim 11, wherein the elements are at least one of disposable bags, disposable containers, filters, hoses, and medical treatment cassettes.

13. The medical treatment arrangement according to claim 1, wherein the data transfer part of the mobile container device is configured to transfer data to at least one of the filling and container devices when the mobile container device approaches the filling or treatment device.

14. The medical treatment arrangement according to claim 1 further comprising
   d) a test device having at least one processor configured to test data transferred from the mobile container device to the filling or treatment device.

15. The medical treatment arrangement according to claim 14 further comprising
   e) a decision device having at least one processor configured to decide based on results of the test whether the medical treatment is carried out or not.

16. The medical treatment arrangement according to claim 1, wherein at least one of the mobile container device and the treatment device further has disposables having machine readable markings.

17. The medical treatment arrangement according to claim 16, wherein the machine readable markings are at least one of a 2D matrix, a barcode, and a RFID tag.

18. The medical treatment arrangement according to claim 1, wherein at least one or the devices has at least one mark identifying at least one of the marked device and the other devices.

19. The medical treatment arrangement according to claim 1, wherein at least one of the devices has at least one interface.

20. The medical treatment arrangement according to claim 19, wherein the at least one interface is at least one of a TFT (LDC) display, an OLED display, and an e-paper display.

21. The medical treatment arrangement according to claim 1, wherein the mobile container device has at least one container configured for receiving at least one of fresh medical treatment fluid, used medical treatment fluid, and substitution fluid.

22. The medical treatment arrangement according to claim 21, wherein at least one of the filling and treatment devices has a flow device configured to fill and empty the at least one container.

23. A medical treatment arrangement comprising
   a) at least one filling device,
   b) at least one treatment device, and
   c) at least one mobile container device reversibly connectable, and movable with respect, to each of the filing and treatment devices,
   wherein the mobile container device an the treatment device are configured to carry out only when connected together the complete medical treatment of a patient,
   wherein each of the devices has an energy-and-data transfer part configured to unidirectionally or bidirectionally transfer energy in a wireless manner to another device sufficient to power, or charge a power supply carried by, the other device, and configured to unidirectionally or bidirectionally transfer data in a wireless manner between the mobile container device and at least one of the filing and treatment devices.

24. The medical treatment arrangement according to claim 23, wherein the energy-and-data transfer part is configured to transfer energy and data in a wireless manner by induction.

25. The medical treatment arrangement according to claim 23, wherein the energy-and-data transfer part is configured to transfer energy and data simultaneously.

* * * * *